(12) United States Patent
Ghilardi et al.

(10) Patent No.: US 9,649,397 B2
(45) Date of Patent: May 16, 2017

(54) STERILIZER

(71) Applicant: NAKANISHI INC., Tochigi (JP)

(72) Inventors: Mariapia Ghilardi, Villa di Serio (IT);
Daniele Ongaro, Villa di Serio (IT)

(73) Assignee: NAKANISHI INC., Tochigi (JP)

(*) Notice: Subject to any disclaimer, the term of this patent is extended or adjusted under 35 U.S.C. 154(b) by 10 days.

(21) Appl. No.: 14/371,626

(22) PCT Filed: Jun. 4, 2013

(86) PCT No.: PCT/IB2013/054588
§ 371 (c)(1),
(2) Date: Jul. 10, 2014

(87) PCT Pub. No.: WO2013/182983
PCT Pub. Date: Dec. 12, 2013

(65) Prior Publication Data
US 2014/0356251 A1 Dec. 4, 2014

(30) Foreign Application Priority Data

Jun. 6, 2012 (IT) .............................. MI2012A0978

(51) Int. Cl.
A61L 2/07 (2006.01)

(52) U.S. Cl.
CPC ........... *A61L 2/07* (2013.01); *A61L 2202/121* (2013.01); *A61L 2202/24* (2013.01)

(58) Field of Classification Search
CPC ......................................................... A61L 2/07
USPC ........................................................ 422/292
See application file for complete search history.

(56) References Cited

U.S. PATENT DOCUMENTS

| 3,261,627 A | 7/1966 | Wallden |
| 5,223,229 A | 6/1993 | Brucker |
| 2002/0085945 A1 | 7/2002 | Florkey et al. |

FOREIGN PATENT DOCUMENTS

| GB | 666 935 A | 2/1952 |
| GB | 1 070 331 A | 6/1967 |
| GB | 2 074 872 A | 11/1981 |
| GB | 2 230 554 A | 10/1990 |
| GB | 2 351 669 A | 1/2001 |

Primary Examiner — Sean E Conley
(74) Attorney, Agent, or Firm — Vorys, Sater, Seymour & Pease LLP

(57) ABSTRACT

Provided is a sterilizer for medical instruments including a sterilization chamber defining an inner space configured for containing medical instruments and pressurized sterilization fluid; a hatch configured to hermetically seal the inner space; a closure system configured to firmly constrain the hatch to the sterilization chamber; at least one discharge valve configured for placing the inner space in connection for fluid passage with an outside space; and a control unit configured to control the discharge valve.

8 Claims, 5 Drawing Sheets

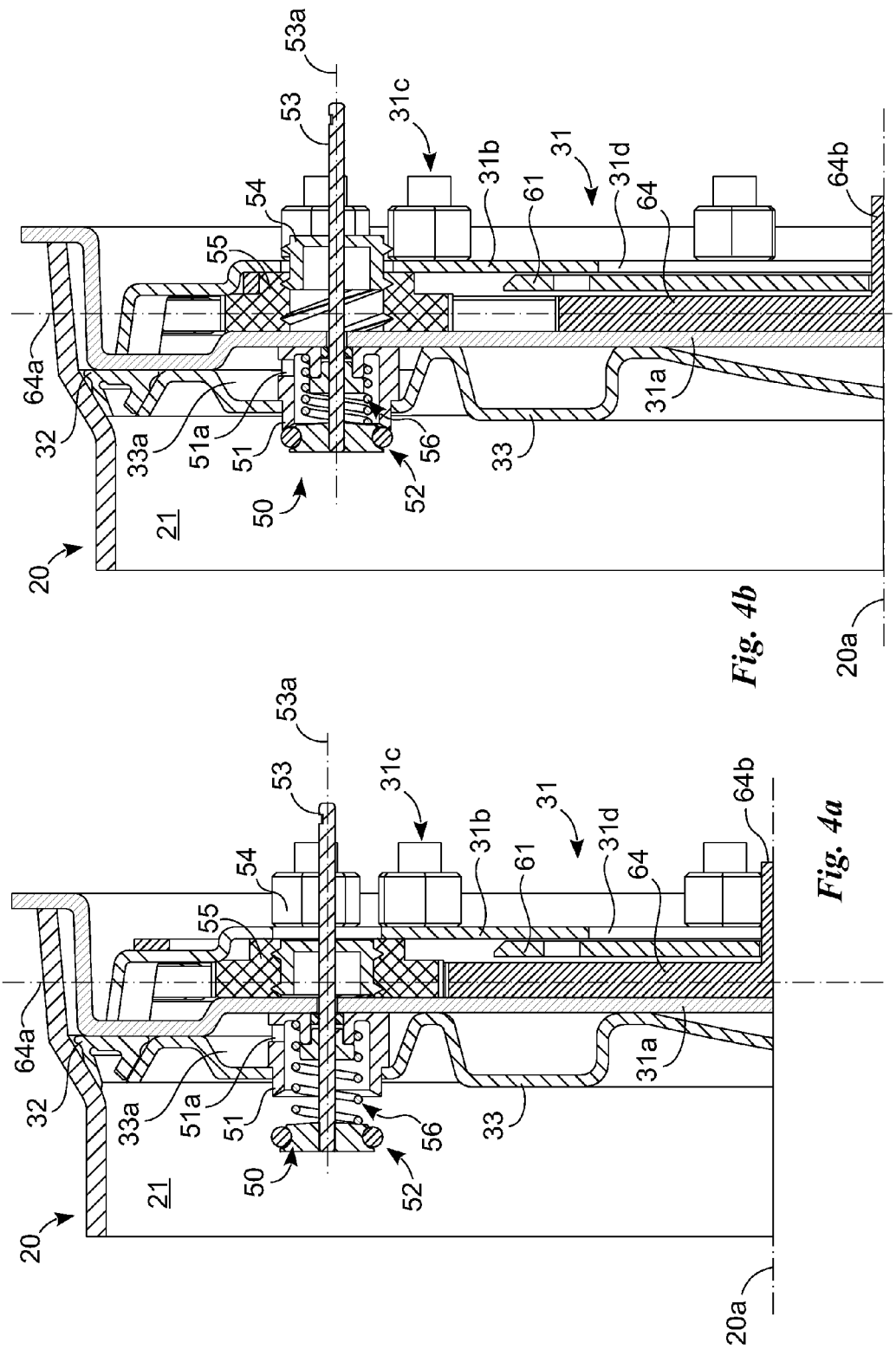

STERILIZER

The present invention relates to a sterilizer of the type as recited in the preamble of the first Claim.

In particular, the invention relates to a steam sterilizer having an inner chamber in which surgical or medical-dental instruments are placed, hereinafter referred to univocally by the expression "medical instruments", so as to be sterilized using a gas, usually water vapour, characterized by high pressure and temperature values.

As is known, in any operation, the use of medical instruments that have been sterilized to a high standard is of fundamental importance in order to prevent infection or other similar problems.

Consequently, before operations the medical instruments are suitably treated in specific sterilizers which by means of chemical substances (ethylene oxide, etc.), ultra violet radiation, plasma or steam, make it possible to lower the bacterial load present on the medical instruments.

Both for economic reasons and because of their sterilizing efficiency currently the most widely used sterilizers are steam sterilizers, also known as autoclaves, since they are particularly economical to manufacture and to use and, above all, are simple to use and can easily be installed in laboratories thanks to their compact size.

The steam sterilizers currently known in the prior art comprise a main tank containing water; a sterilization chamber defining an inner space for placing the instruments to be sterilized; a hatch suitable to be moved so as to alternately permit easy access to the inner space or to make such space airtight to pressurised gas; a feeding system suitable to draw water from the main tank, convert it into steam and convey such steam into the sterilization chamber; drying means, suitable to dry the equipment using, for example, a jet of hot air; and an evacuation system suitable to expel the waste fluid, that is the liquid and the residual gas/steam from the sterilization process.

The prior art described above has several significant drawbacks.

A first significant drawback is represented by the fact that the steam sterilizers currently in use are very heavy, complex and expensive.

Said sterilizers must in fact withstand high internal pressures. In particular the hatch of the known sterilizer is heavy and complex and absorbs a large amount of heat.

Said hatch must, in addition ensure a high level of safety to prevent the steam, on account of its high pressure and temperature, from constituting a hazard for the operator.

In this situation the technical purpose of the present invention is to devise a sterilizer able to substantially overcome the drawbacks mentioned above.

Within the sphere of said technical purpose one important aim of the invention is to make a sterilizer able to guarantee a high level of safety.

Another important aim of the invention is to create a simple, economical and structurally lightweight sterilizer.

The technical purpose and specified aims are achieved by a sterilizer as claimed in the appended Claim 1.

Preferred embodiments are described in the dependent claims.

The characteristics and advantages of the invention are clearly evident from the following detailed description of a preferred embodiment thereof, with reference to the accompanying drawings, in which.

Figure 1:
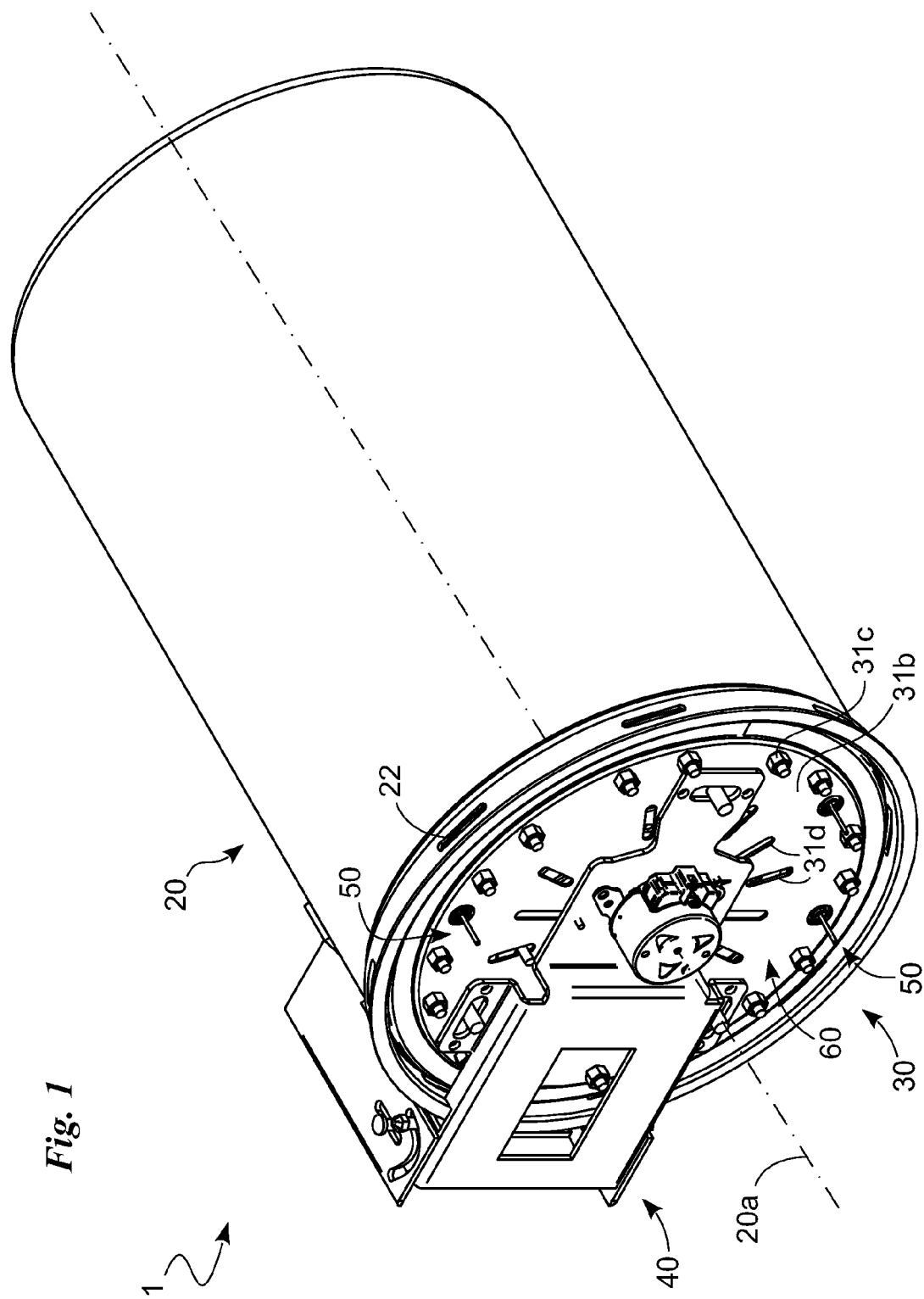
FIG. 1 shows a sterilizer according to the invention.
Figure 2B:
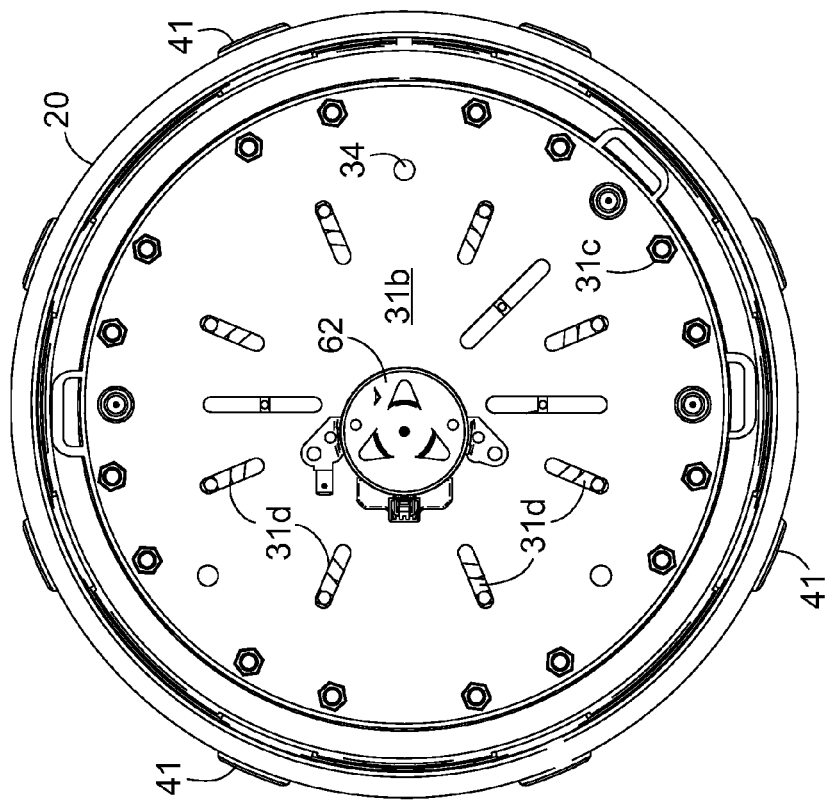
FIGS. 2a-2b show a component of the sterilizer in two different configurations.
Figure 2A:
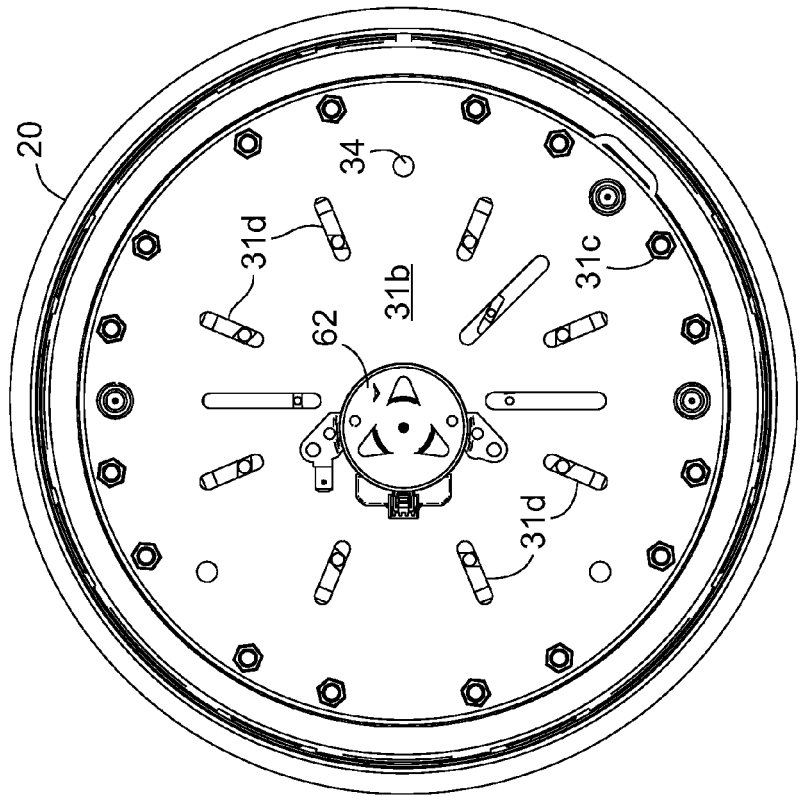
Figure 3A:
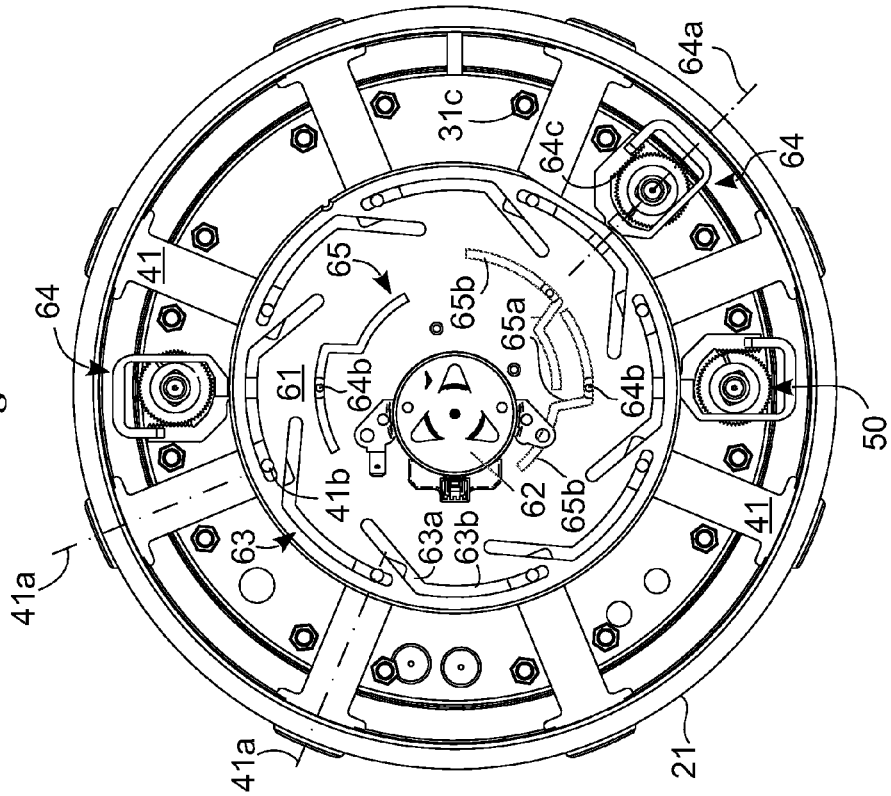
FIGS. 3a-3b show two cross-sections of the component in FIGS. 2a-2b in the configurations shown in such figures.
Figure 3B:
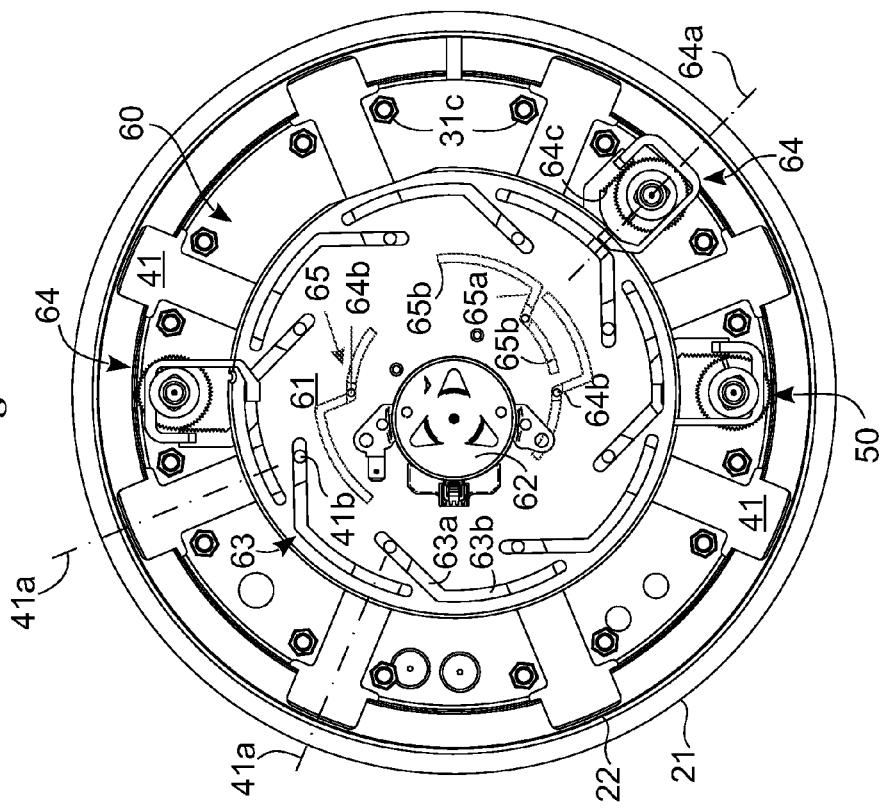
Figure 5A:
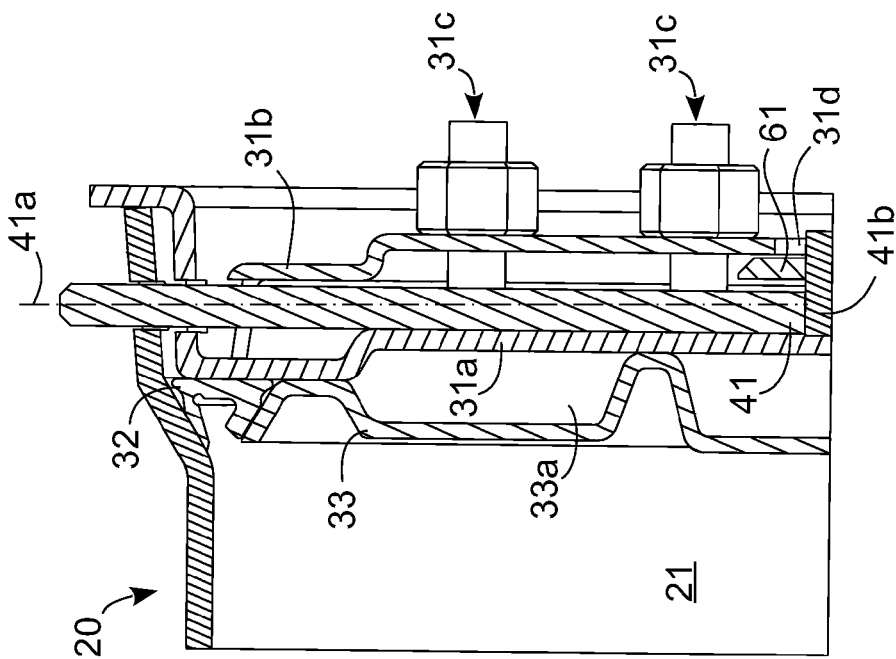
Figure 5B:
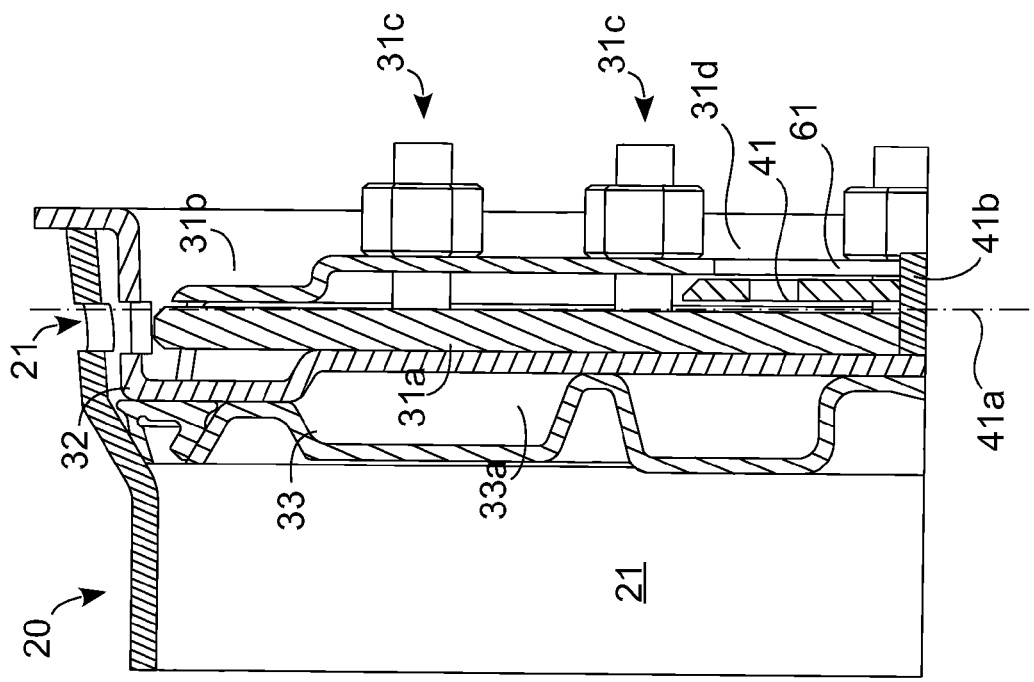

FIGS. 4a-4b present two partial views of a portion in cross-section of the component in FIGS. 2a-2b; and FIGS. 5a-5b present two partial views of a further portion in cross-section of the component in FIGS. 2a-2b.

Referring to said drawings, reference numeral 1 globally denotes the sterilizer according to the invention.

It is suitable to use a pressurised fluid to sterilize medical instruments and medical-dental instruments such as, for example, forceps, surgical scissors, clamps, shears and needles. In particular, the sterilizer 1 is suitable for performing the sterilization of medical instruments using a gas, and more specifically, water vapour at suitable pressure and temperature values.

The sterilizer 1 comprises a sterilization chamber 20 defining a main extension axis 20a and an inner space 21 suitable to house the medical instruments; a hatch 30 suitable to be joined, preferably hinged, to the sterilization chamber 20 so as to hermetically seal the inner space 21; a closure system 40 suitable to firmly constrain the hatch 30 to the sterilization chamber 20; one or more discharge valves 50 suitable to place the inner space 21 into connection for fluid passage with the outside, that is with the outside environment or another device suitable to collect the fluid in output from the sterilization chamber 20 permitting its re-use.

The closure system 40 comprises one or more engagement teeth 41 each of which suitable to engage itself in a housing 22 made in the sterilization chamber 20, thus constraining the hatch 30 to said chamber 20.

The engagement teeth 41, when inserted in the housings 22, are suitable to structurally completely constrain the hatch 30 to the chamber 20 therefore, without the help of a hinge or the like, and to withstand the thrust of the pressurised vapour. These are therefore placed with a circumferential symmetry along the rims of the hatch 30.

In particular a number of four to twelve and preferably eight engagement teeth are present, positioned with circumferential symmetry so as to ensure the correct closing of the hatch 30.

The sterilizer 1 has discharge valves 50 which are constrained to the hatch and, in particular, to the hatch 30, each of which comprises a duct 51 suitable to be crossed by the sterilization fluid; an occlusion element 52 suitable to engage with said duct 51 preventing the passage of fluid through it; and an aperture apparatus suitable to vary the distance of said occlusion element 52 from the duct 51 so as to alternately open or close the valve 50.

In detail, the aperture apparatus comprises stem 53 integral with the occlusion element 52 and defining a direction of extension 53a, preferably substantially parallel to the extension axis 20a; a sliding element 54 integral with the stem 53; a command element 55 coupled by means of an inner thread to the sliding element 54 so as to move the stem 53 substantially along the direction of extension 53a; and elastic means 56 suitable to permit the correct aperture or closure of the valve 50.

As well as said components, the sterilizer 1 comprises a control unit 60 suitable to control both the discharge valves 50 and the closure system 40; a filling/emptying apparatus not shown in the drawings, suitable to ensure the correct flow of sterilization fluid in the chamber 20.

In detail, the control unit 60 is kinematically connected to the discharge valves 50 and to the closure system 40 in such a way as to mechanically control said discharge valves 50 and said closure system 40.

Such mechanical connection between the discharge valves 50, closure system 40 and control unit 60 permits the sterilizer 1 to advantageously define, an open configuration (FIGS. 2*a*, 3*a*, 4*a*, 5*a*) in which the hatch 30 is movable in relation to the sterilization chamber 20 and in which the discharge valves 50 form the connection for fluid passage between the inner space 21 and the outside; and a closed configuration (FIGS. 2*b*, 3*b*, 4*b*, 5*b*) in which the hatch 30 is firmly constrained to the chamber 20 and wherein the valves 50 prevent the aforesaid connection for fluid passage.

In particular, in the closed configuration, the control unit 60 makes the engagement teeth 41 protrude at least partially from the hatch 30 so as to engage the housings 22 and firmly constrain the cover 30 to the chamber 20, while, in the open configuration, the unit 60 forces the teeth 41 to be housed practically totally in the hatch 30 which is thus mobile in relation to the chamber 20.

Moreover, it suitably defines an intermediate configuration, advantageously forcibly positioned between the open and closed configurations, in which the discharge valves 50 permit the connection for fluid passage between the inner space 21 and outside and wherein the hatch 30 is firmly constrained to the sterilization chamber 20. Said intermediate configuration is forcibly positioned in the sense that it is not possible to pass between said open and closed configurations, and, in particular from the closed configuration to the open configuration, without passing through the intermediate configuration.

In detail, the control unit 60 orders the forced passage between the configurations and thus, an activation of the discharge valves 50 and closure system 40 according to a given sequence, that is, when the sterilizer 1 is open, the sequence is the closed, intermediate and lastly open configuration; while, when the sterilizer is closed, the sequence is the open, intermediate and lastly closed configuration.

The control unit 60 (FIGS. 3*a*-3*b*) thus comprises a maneuvering member 61 kinematically connected both to the engagement teeth 41 and to the discharge valves 50 so as to control the change of configuration of the sterilizer 1; and a motor 62, appropriately electric, suitable to move the maneuvering member 61 so as to vary the configuration of the sterilizer 1. In particular, the motor 62 rotates the maneuvering member 61 in relation to an axis substantially parallel to the main extension axis 20*a*.

The maneuvering member 61, so as to be connected to each engagement tooth 41, has one or more guides 63 joined to the engagement teeth 41 so as to substantially simultaneously move the teeth 41 along slide directions 41*a* transversal to the main extension axis 20*a*.

Preferably, the guides 63 consist of through cavities in which pins 41*b* integral with the teeth 41 are inserted and which define slide directions 41*a* substantially radial to the main extension axis 20*a* and, even more preferably, lying on a plane substantially perpendicular to the extension axis 20*a*. Alternatively, the slide directions 41*a* are inclined in relation to the axis 20*a* so that the advancement motion of the teeth 41 presents a component entering the space 21, and consequently the hatch 30 is pressed against the chamber 20 ensuring a hermetic closure.

To permit the definition of the aforementioned configurations, each guide 63 innovatively comprises at least two separate portions: a first portion 63*a* suitable to vary the distance of the pin 41*b* and thus of the tooth 41 from the main extension axis 20*a* during the rotation of the maneuvering member 61; and a second portion 63*b* suitable to enable the engagement teeth 40 to remain substantially stationary during the rotation of the maneuvering member 61.

Preferably, the first portion 63*a* has an extension line substantially transversal to the slide direction 41*a* while the second portion 63*b* is an arched shape with its centre substantially lying on the direction of extension 20*a*.

In order to define the intermediate configuration, the control unit 60 has one or more activation blocks 64 suitable to selectively control the opening or closing of the discharge valves 50 and one or more additional guides 65, preferably through cavities made in the maneuvering block 61, engaged with the blocks 64 so as to move them in additional slide directions 64*a*. In particular, the addition slide directions 64*a* are positioned substantially radially to the main extension axis 20*a*, and even more preferably, lie on a plane substantially perpendicular to the extension axis 20*a*.

The activation blocks 64 have an additional pin 64*b* suitable to engage with an additional guide 65 and a ring nut 64*c* suitable to engage with the outer thread of the control element 55 so as to command its rotation.

Each of the additional guides 65 comprises a first additional portion 65*a* suitable to vary the distance of the additional pin 64*b* and thus of the activation block 64 from the main extension axis 20*a*, and one or more second additional portions 65*b* suitable to permit the blocks 64 to remain substantially stationary during the rotation of the maneuvering member 61.

Preferably, the first additional portion 65*a* has an extension line substantially transversal to the additional slide direction while the second additional portions 65*b* have an arched shape with their centre substantially lying on the direction of extension 20*a*.

The additional guides 65 and, in particular, the first additional portions 65*a*, in order to have a sequential opening of the discharge valves 50, are reciprocally distanced according to angles of aperture, calculated in relation to the main extension axis 20*a*, different from those present between the discharge valves 50.

In particular, to ensure such gradual release, two discharge valves 50 may be controlled by means of a single additional guide 65, as shown in FIGS. 4*a*-4*b*.

To ensure the correct movement of the engagement teeth 41 and of the activation blocks 64 along the slide directions 41*a* and 64*a*, the hatch 30 comprises a main framework 31 suitable to enclose within it the engagement teeth 41 and the blocks 64 defining, for such elements, slide channels substantially parallel to the slide directions 41*a* and 64*a*.

The main framework 31 comprises two reinforcements, one inner 31*a* and one outer 31*b*, that is respectively facing the inner space 21 and the outside of the sterilizer 1, reciprocally connected by means of bolts 31*c*, welding or other means of constraint. Preferably, the outer reinforcement 31*b* has slide channels 31*d*, having appropriately a substantially radial extension in relation to the main extension axis 20*a*, inside which the pins 41*b* and 64*b* slide as the configurations of the sterilizer 1 change.

The hatch 30 further comprises a gasket 32 suitable to position itself between the first reinforcement 31*a* and the sterilization chamber 20 so as to hermetically seal the inner space 21; and a plate 33 constrained to the framework and, in particular, to the inner plate 31*a* so as to position itself between it and the inner spaces 21.

In particular, the plate 33 is appropriately shaped in order to define, together with the inner reinforcement 31*a*, at least one channel 33*a* suitable to place in connection for fluid passage the discharge valves 50 and, in particular, the ducts 51, by opening 51*a*, and to permit the valves 50 to discharge the sterilization fluid outwards through the holes 34 made in the reinforcements 31*a* and 31*b* (FIGS. 2*a*-2*b* and 4*a*-4*b*).

The functioning of a sterilizer, described above in a structural sense, is as follows.

Initially, the sterilizer 1 is in the open configuration, that is, with the hatch 30 movable in relation to the sterilization chamber 20 and with the discharge valves 50 open.

At the moment in which sterilization is to be performed, the operator places the medical instruments in the inner space 21, brings the hatch 30 into contact with the sterilization chamber 20, and using the control unit, selectively controls the valves 50 and the closure system 40 so that the sterilizer 1 moves into the closed configuration, after the appropriate command from the operator.

In detail, the control unit 60, by means of the maneuvering member 61, commands the hermetic closure of the sterilization chamber 20 by means of the hatch 30 leaving the discharge valves 50 open (sterilizer 1 in intermediate configuration) and, subsequently closing the valves 50 (sterilizer 1 in the closed configuration)

In detail, during such action, the motor 62 places the maneuvering member 61 in rotation substantially around the main extension axis 2*a* making the pins 41*b* and the additional pins 64*b* slide respectively in the guides 63 and in the additional guides 65.

Thanks to such rotation, the pins 41*b* encounter the first portion 63*a* while the additional pins 64*b* slide inside the corresponding second additional portions 65*b* making the engagement teeth 41 move along slide directions 41*a* while the activation blocks 64 and, as a result, the discharge valves 50 remain substantially unchanged.

As a result of such situation the engagement teeth 41 begin to protrude from the main framework 31 and to insert themselves in the housings 22 constraining the hatch 30 to the sterilization chamber 20 and, thereby, placing the sterilizer 1 in the intermediate configuration.

Once the intermediate configuration has been reached, the rotation of the maneuvering member 61 continues, bringing the sterilizer 1 into the closed configuration.

In particular, the rotation of the maneuvering member 61 makes the pins 41*b* and the additional pins 64*b* slide respectively in the second portions 63*b* and in the first additional portions 65*a* so that the teeth 40 remain substantially stationary while the activation blocks 64 move along additional slide directions.

Such translation of the ring-nuts 64*c*, said ring-nuts being engaged by the control elements 55, causes the translation of the occlusion elements 52 along the direction of extension 53*a* and thus the closure of the valves 50.

Having thus achieved the closed configuration, the operator orders the sterilization of the medical instruments and then the return to the initial open configuration.

During such return, the maneuvering member 61 is rotated in the opposite direction to previously so that while the pins 41*b* slide in the second portions 63*b*, the additional pins 64*b* move along the first portions 65*a* determining the translation of the activation blocks 64 and the opening of the discharge valves 50.

After reaching the intermediate configuration, the sterilization fluid flows inside the ducts 51, along the channel 32*a* and then comes out through the holes 34.

Simultaneously, the maneuvering member 61, continuing its rotation makes the pins 41*b* slide in the first portions 63*a* and the additional pins 64*b* in the second portions 65*b* so that, while the activation blocks 64 remain substantially stationary, the teeth disengage from the housings 22 permitting the opening of the sterilizer 1.

The invention achieves some important advantages.

A first important advantage is the high level of safety guaranteed by the sterilizer 1, ensured thanks to the particular opening/closing sequences characterizing said sterilizer.

In fact, the presence of an intermediate configuration, in which the hatch 30 is firmly constrained to the chamber 20 while the discharge valves 50 are open, ensures that the pressure inside said chamber is advantageously discharged outside before the hatch 30 is opened.

Another advantage is the mechanism which permits activation in the correct sequence of the opening of the discharge valves 50 and the opening of the sterilizer 1.

In particular, the fact that such sequence is obtained mechanically prevents the operator from opening the sterilizer directly to speed up the sterilization process, without having first correctly drained the sterilization fluid.

The aforesaid improved safety is also ensured by the fact that the sterilization device permits a non-simultaneous opening of the discharge valves 50 and thus, optimal control of the sterilization fluid in output from the sterilizer 1.

One important advantage is also given by the presence of the channel 33*a* which, by permitting channelling of the flow in output from the sterilizer, permits its optimal channelled emptying, reducing the use of expensive piping and making the sterilizer 1 more efficient.

Yet another important advantage lies in the fact that the engagement teeth 41, when inserted in the housings 22, are suitable to structurally completely constrain therefore, without the help of a hinge or the like, the hatch 30 to the chamber 20 and to withstand the thrust of the pressurised vapour. Such characteristic in fact leads to a lightening of said hatch 30 and a simplification of the sterilizer, which does not require very expensive and complex load-bearing hinges.

Moreover, the channelling of the gas from inside outwards makes it possible to prevent the so-called risk of backflow, that is to say the risk that non-sterile external gases may enter the chamber at the moment of opening the hatch.

Variations may be made to the invention described herein without departing from the scope of the inventive concept expressed in the independent claims.

For example, the opening of the valves 50 may take place in an intermediate step of opening the hatch in a perpendicular direction to the plane of said hatch. In such intermediate step the hatch 30 permits the passage of steam through the perimetral gasket, appropriately designed to permit the channelling of the gases in such step. In the subsequent step the hatch is opened and gives free access to the chamber.

All the elements as described and claimed herein may be replaced with equivalent elements and the scope of the invention includes all other details, materials, shapes and dimensions.

The invention claimed is:
1. A sterilizer for medical instruments, comprising:
 a sterilization chamber defining an inner space configured for containing medical instruments and pressurised sterilization fluid and a main extension axis;
 a hatch configured to hermetically seal the inner space;
 a closure system configured to firmly constrain said hatch to said sterilization chamber, comprising at least one discharge valve configured for placing said inner space in connection for fluid passage with an outside space and at least one engagement tooth; and a control unit configured to control both said at least one discharge valve, and said closure system,
wherein said closure system defining
an open configuration in which said hatch is movable in relation to said sterilization chamber and said at least one discharge valve forms said connection for fluid passage between said inner space and said outside space,
a closed configuration in which said hatch is firmly constrained to said sterilization chamber and in which said at least one discharge valve prevents said connection for fluid passage between said inner space and said outside space, and
an intermediate configuration, forcibly positioned between said open configuration and said closed configuration, in which said at least one discharge valve permits said connection for fluid passage between said inner space and said outside space and in which said hatch is firmly constrained to said sterilization chamber,
wherein said control unit also comprises a maneuvering member kinematically connected to said at least one engagement tooth so as to move said at least one engagement tooth along an actuation direction transverse to said main extension axis, wherein, in said closed configuration, said at least one engagement tooth protrudes from said hatch engaging at least one housing made in said sterilization chamber and that in said open configuration, said at least one engagement tooth is substantially totally housed in said hatch,
said maneuvering member is kinematically connected to said at least one discharge valve so that, depending on the movement of said maneuvering member, the opening or closing of said at least one discharge valve is selectively commanded.

2. The sterilizer as claimed in claim 1, said at least one engagement tooth, when inserted in said at least one housing, is configured to structurally completely constrain said hatch to said chamber.

3. The sterilizer as claimed in claim 1, said control unit further comprising a maneuvering member comprising at least one guide associated with said at least one engagement tooth, wherein said maneuvering member is configured to rotate in relation to an axis substantially parallel to said main extension axis defining said actuation direction positioned substantially radially to said main extension axis.

4. The sterilizer as claimed in claim 3, said at least one guide further comprising a first slide portion having an extension line substantially transversal to said main extension axis so as to permit said at least one engagement tooth to translate in relation to said main extension axis.

5. The sterilizer as claimed in claim 3, said at least one guide further comprising a second portion having an arched shape with its centre lying substantially on said main extension axis.

6. The sterilizer as claimed in claim 1, said control unit further comprising at least one activation block configured for connecting said maneuvering member to said discharge valve; in which said maneuvering member comprising at least one additional guide associated to said at least one activation block so as to move said at least one activation block along an additional slide direction placed substantially radially to said main extension axis.

7. The sterilizer as claimed in claim 6, comprising a plurality of said discharge valves; wherein said maneuvering member further comprising a plurality of said additional guides, each of said additional guides comprising a first additional portion configured to move said at least one activation block in relation to said main extension axis, and said first additional portions are reciprocally distanced according to angles of aperture different from the angle of aperture of said discharge valves.

8. The sterilizer as claimed in claim 1, wherein said hatch, comprises:
a framework, and
a plate constrained to said framework so as to define at least one channel configured for placing in connection for fluid passage said discharge valves and a duct suitable to be crossed by the sterilization fluid.

* * * * *